United States Patent [19]

Dhabhar

[11] 4,289,755

[45] Sep. 15, 1981

[54] STABLE MOUTHWASH COMPOSITIONS CONTAINING ZINC AND FLUORIDE COMPOUNDS

[75] Inventor: Dadi J. Dhabhar, Norwalk, Conn.

[73] Assignee: Richardson-Vicks Inc., Wilton, Conn.

[21] Appl. No.: 203,634

[22] Filed: Nov. 3, 1980

[51] Int. Cl.³ .................... A61K 7/16; A61K 7/18; A61K 7/24

[52] U.S. Cl. ........................ 424/52; 424/49; 424/55

[58] Field of Search ...................... 424/49–58

[56] References Cited

U.S. PATENT DOCUMENTS

| | | | |
|---|---|---|---|
| 3,772,431 | 11/1973 | Mlkvy et al. | 424/49 |
| 3,888,976 | 6/1975 | Mlkvy et al. | 424/49 |
| 4,022,880 | 5/1977 | Vinson et al. | 424/49 |
| 4,082,841 | 4/1978 | Pader | 424/52 |
| 4,100,269 | 7/1978 | Pader | 424/49 |
| 4,138,477 | 2/1979 | Gaffar | 424/52 |
| 4,144,323 | 3/1979 | Lamberti | 424/49 |
| 4,152,418 | 5/1979 | Pader | 424/50 |
| 4,154,815 | 5/1979 | Pader | 424/50 |
| 4,229,430 | 10/1980 | Fahim et al. | 424/49 |

Primary Examiner—Shep K. Rose
Attorney, Agent, or Firm—George W. Rauchfuss, Jr.

[57] ABSTRACT

A stable mouthwash composition is provided with acceptable astringency and without loss of anti-odor properties, and improved compatibility with fluoride ions.

7 Claims, No Drawings

STABLE MOUTHWASH COMPOSITIONS CONTAINING ZINC AND FLUORIDE COMPOUNDS

FIELD OF THE INVENTION

This invention relates to novel and stable mouthwash compositions containing both zinc and fluoride compounds.

BACKGROUND OF THE INVENTION

The beneficial effect of zinc compounds in dental compositions, especially in toothpastes and mouthwashes, has been generally recognized for some time. In U.S. Pat. No. 4,100,269, issued July 11, 1978 to Morton Pader, there is disclosed the use of insoluble zinc compounds in dentifrices for improving the control of calculus. Insoluble zinc compounds employed in the patent are those having a solubility of less than about one gram of zinc per 100 cc of water at 20° C. and preferably a solubility of not more than about 0.5 gram zinc compound per 100 cc water at 20° C. Among the typical insoluble zinc compounds employed in the patent is zinc citrate. In U.S. Pat. No. 4,138,477, issued Feb. 6, 1979, to Maria Gaffar, there is disclosed composition for preventing and controlling mouth odor containing a zinc-polymer combination of a zinc compound and an anionic polymer. Also it has been known to formulate tooth powders containing zinc citrate and calcium gluconate such as disclosed in U.S. Pat. No. 1,861,189 issued May 31, 1932 to Charles Pfizer.

In addition, zinc chloride has been used in mouthwash compositions and recognized as possessing anti-mouth odor properties in said compositions. In U.S. Pat. No. 2,527,686, issued Oct. 31, 1959, to Max Sandberg, a mouthwash containing zinc chloride and an alkali metal or ammonium fluoride which also contains papain, malt and formalin is disclosed. However, the zinc chloride is not really very stable in such a formulation and the necessity to include formalin, papain and malt is not desirable. Moreover, a zinc chloride mouthwash is stable only at an acid pH of about 3.

However, despite the heretofore known use of zinc compounds in dental compositions their use has not been without certain undesirable drawbacks and side-effects. For example, when such zinc compounds have been employed it has not been possible to satisfactorily include ionic fluoride in the compositions due to the chemical incompatibility therebetween. A sodium fluoride mouthwash must have a pH in the neutral range since at acidic pH the enamel solubility of teeth is increased resulting in increased tooth decay. Moreover, while zinc chloride possesses the desired anti-odor activity, its high level of astringency is undesirable. Yet other zinc compounds, such as for example, zinc citrate are so slightly soluble in aqueous solutions that while the level of astringency is kept acceptably low, there is an undesirable loss in anti-mouth odor activity of the zinc compound.

It is therefore highly desirable to provide a mouthwash composition that is less astringent than zinc chloride so as to provide enhanced acceptance by users of dental compositions containing same yet without sacrificing anti-odor activity. It is also desirable to provide a stable mouthwash composition containing a zinc compound not as astringent as zinc chloride but which does not present substantially any chemical incompatibility problem in dental compositions employing an ionic fluoride compound.

BRIEF DESCRIPTION OF THE INVENTION

In accordance with the invention a novel stable mouthwash composition is provided that contains zinc citrate, citric acid and sodium fluoride and in which an alkali compound has been added to adjust the pH of the composition to a pH of 6.0 to 7.2, preferably 6.5 to 7.2.

DETAILED DESCRIPTION OF THE INVENTION

A stable mouthwash composition containing both zinc and fluoride compounds is prepared by employing zinc citrate, sodium fluoride with the addition of an alkali compound, preferably an alkali metal or ammonium hydroxide and most preferable sodium hydroxide in an amount sufficient to adjust the pH of the mouthwash to the neutral range of pH 6.0 to 7.2., preferably 6.5 to 7.2.

The sodium fluoride, zinc citrate and citric acid can be employed in any suitable mouthwash vehicle provided the mouthwash can have its pH adjusted to pH 6.0 to 7.2 by the addition of an alkali compound, especially sodium or potassium hydroxide. The new stable mouthwash compositions of this invention are less astringent than zinc chloride containing mouthwash compositions and, therefore, are of greatly enhanced acceptability yet without sacrificing anti-odor property.

The zinc citrate component of the mouthwash can be provided by employing zinc citrate or by the formation of zinc citrate in situ in the mouthwash, such as by employing zinc chloride and citric acid in amounts sufficient to react to form the required amount of zinc citrate.

In mouthwash compositions of this invention zinc citrate is employed in amounts of from about 0.1 to about 15.0%, preferably about 0.2 to about 5%, and most preferably about 0.2 to about 2.0%, by weight based on the total weight of the composition so as to provide from about 7 to about 28 mg/kg body weight of the user thereof. The sodium fluoride is employed in the mouthwash compositions in an amount within the range of from about 0.01 to about 1% by weight. The mouthwash compositions of the present invention comprise the aforesaid zinc citrate, citric acid, sodium fluoride and alkali compound and a mouthwash carrier suitable for use in the oral cavity. The carrier can be water or an organic solvent such as alcohol.

The citric acid in the mouthwash composition is required to solvate the zinc citrate compound. The amount of citric acid employed will be a amount sufficient to solvate the zinc citrate and ideally is in a molar ratio of 1 mole zinc citrate to 2.76 moles citric acid. However, the amount of citric acid that can be used to solvate the zinc citrate can range from about 1.5 to 10 molar, preferably about 2.25 to 10 molar, and most preferable from about 2.5 to 3.5 molar, relative to 1 mole of zinc citrate.

Mouthwashes generally comprise a water/ethyl alcohol solution and optionally other ingredients such as flavor, sweeteners, and humectants. The alcohol provides an antibacterial effect. Optionally, mouthwashes also contain sudsing agents. Humectants such as glycerine and sorbitol give a moist feel in the mouth and are desirably also present. Antibacterial agents are sometimes incorporated into mouthwashes or dentifrices at levels from about 0.01% to about 2.0% by weight.

Generally, mouthwashes suitable for use as carriers herein contain: 5% to 40% ethyl alcohol; 0% to 20%, preferably 5% to 20%, glycerine or other humectant; 0% to 12%, preferably 0.1% to 12%, sudsing agent, 0% to 0.5%, preferably 0.05% to 0.5%, sweetening agent such as saccharin; and 0% to 0.3%, preferably 0.05% to 0.3%, flavoring agent; and the balance, water with colorants or dyes if desired.

Mouthwashes usually contain surface-active agents also called sudsing agents. Suitable surface-active agents are those which are reasonably stable and form suds throughout a wide pH range, that is, nonsoap nonionic, cationic, and amphoteric organic synthetic detergents.

The nonionic synthetic detergents which can be used with the mouthwash compositions of the present invention may be broadly defined as compounds produced by the condensation of a hydrophilic alkylene oxide group with an organic hydrophobic compound which may be aliphatic or alkyl-aromatic in nature. The length of the hydrophyllic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with a hydrophobic base formed by the condensation of propylene oxide with propylene glycol.

Other suitable nonionic synthetic detergents include: the polyethylene oxide condensates of alkyl phenols, those derived from the condensation of ethylene oxide with the product resulting from the reaction of propylene oxide and ethylene diamine, the condensation product of aliphatic alcohols having from 8 to 18 carbon atoms, in either straight chain or branched chain configuration, with ethylene oxide, and the polyoxyethylene derivatives of fatty acid partial esters of sorbitol anhydride and available in the market under the trade name "Tween."

Cationic synthetic detergents useful in the mouthwash compositions of the present invention can be broadly defined as quaternary ammonium compounds having one long alkyl chain containing from about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconutalkyltrimethylammonium nitrite, cetyl pyridinium fluoride, and the like.

The amphoteric synthetic detergents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, for example, carboxylate, sulfonate, sulfate, phosphate, or phosphonate.

Many additional nonionic, cationic and amphoteric synthetic detergents are known to the art and can be used as sudsing agents in the compositions herein. Further examples can be found in *McCutcheon's Detergents and Emulsifiers*.

The sudsing agent can be employed at levels ranging from about 0.5% to about 5.0% by weight of the mouthwash composition.

Mouthwashes normally also contain flavoring agents. Suitable flavoring agents for use in the mouthwashes herein include, for example, wintergreen oil (methyl salicylate), oil of peppermint, oil of sassafras (synthetic), and oil of anise. Flavoring agents are present at a level of from 0.01% to 2.0% by weight.

Mouthwashes normally also contain sweetening agents. Suitable sweetening agents for use in mouthwashes include for example saccharin, dextrose and levulose. The sweetening agents are used at levels of from about 0.05% to about 2% by weight.

As examples of stable mouthwash formulation of this invention reference may be had to the following exemplary formulation.

FORMULATION

A mouthwash in accordance with the present invention is formulated as follows:

| Component | Amounts per 2 liter |
|---|---|
| Ethyl alcohol (95% in water) | 105.6 ml |
| Glycerine | 40.0 ml |
| Pluronic F-127 | 20.0 g |
| Tween 80 | 1.0 g |
| Sodium hydroxide (10% in water) | 26.0 ml |
| Insoluble saccharin | 1.16 g |
| Flavoring | 2.72 g |
| Citric acid, hydrous | 6.14 g |
| Sodium fluoride | 1.0 g |
| Zinc citrate | 6.46 g |
| Colorant | 20.0 ml |
| Distilled water | balance to two liters |

The mouthwash is prepared by adding to the distilled water the indicated amounts of citric acid, zinc citrate, sodium fluoride and glycerine. To the alcohol there is added the indicated amounts of Pluronic F-127, Tween 80, saccharin and flavoring. The alcohol and water solutions are then combined, the colorant added and mixed. The pH of the mouthwash is then adjusted, by the addition of sufficient sodium hydroxide, to a pH of 7.0

I claim:

1. A stable mouthwash composition containing zinc and fluoride compounds comprising a mouthwash carrier, from about 0.1 to about 15% by weight zinc citrate, from about 0.01 to about 1% by weight sodium fluoride, an amount of citric acid sufficient to solvate the zinc citrate and an amount of an alkali compound sufficient to adjust the pH of the mouthwash composition to a pH within the range of pH 6.0 to 7.2.

2. A stable mouthwash composition of claim 1 wherein the amount of citric acid present is an amount of from about 1.5 to about 10 moles citric acid per 1 mole of zinc citrate.

3. A stable mouthwash composition of claim 2 wherein the amount of citric acid present is an amount of from about 2.5 to about 3.5 moles per 1 mole of zinc citrate.

4. A stable mouthwash composition of claim 3 wherein the amount of citric acid present is an amount of about 2.76 moles per 1 mole of zinc citrate.

5. A mouthwash composition of claim 3 wherein the alkali compound is an alkali metal or ammonium hydroxide.

6. A mouthwash composition of claim 5 wherein the alkali compound is sodium hydroxide.

7. A mouthwash composition of claim 6 wherein the mouthwash carrier comprises about 5 to 40% by weight ethyl alcohol, about 0 to 20% by weight humectant, about 0 to 12% by weight surface active agent, about 0 to 0.5% by weight sweetening agent, about 0 to 0.31% by weight flavoring agent, and the balance distilled water.

* * * * *